(12) United States Patent
Jin

(10) Patent No.: US 12,103,981 B2
(45) Date of Patent: Oct. 1, 2024

(54) METHODS AND COMPOSITIONS RELATING TO ANTI-BIOTIN ANTIBODIES

(71) Applicant: Wayne State University, Detroit, MI (US)

(72) Inventor: Jian-Ping Jin, Chicago, IL (US)

(73) Assignee: Wayne State University, Detroit, MI (US)

( * ) Notice: Subject to any disclaimer, the term of this patent is extended or adjusted under 35 U.S.C. 154(b) by 918 days.

(21) Appl. No.: 17/264,459

(22) PCT Filed: Aug. 2, 2019

(86) PCT No.: PCT/US2019/044851
§ 371 (c)(1),
(2) Date: Jan. 29, 2021

(87) PCT Pub. No.: WO2020/028776
PCT Pub. Date: Feb. 6, 2020

(65) Prior Publication Data
US 2021/0317232 A1    Oct. 14, 2021

Related U.S. Application Data

(60) Provisional application No. 62/713,677, filed on Aug. 2, 2018.

(51) Int. Cl.
*C07K 16/44*    (2006.01)
*G01N 33/68*    (2006.01)

(52) U.S. Cl.
CPC ......... *C07K 16/44* (2013.01); *G01N 33/6854* (2013.01); *C07K 2317/92* (2013.01)

(58) Field of Classification Search
CPC .... C07K 16/44; C07K 2317/92; G01N 33/53; G01N 33/58; G01N 33/6854
See application file for complete search history.

(56) References Cited

FOREIGN PATENT DOCUMENTS

CN    102539790 A    7/2012

OTHER PUBLICATIONS

Kim et al., "Generation, Diversity Determination, and Application to Antibody Selection of a Human Naïve Fab Library," Mol. Cells, 2017, vol. 40, No. 9, pp. 655-666.*
Vincent, P. et al. A comparison of the binding of biotin and biotinylated macromolecular ligands to an anti-biotin monoclonal antibody and to streptavidin, Journal of Immunological Methods, 165:177-182, 1993.
International Search Report and Written Opinion for PCT/US2019/044851 dated Nov. 28, 2019.

* cited by examiner

*Primary Examiner* — Galina M. Yakovleva
(74) *Attorney, Agent, or Firm* — Julie K. Staple; Dinsmore & Shohl LLP

(57) ABSTRACT

Increasingly, human subjects are taking biotin as a medical therapy or nutritional supplement. This practice causes difficulty in analysis of biological samples, such as blood samples, using biotin conjugate reagents since free biotin results in interference. Inventive antibodies, and antigen binding fragments thereof, which specifically bind to biotin of a biotin conjugate and which have a higher affinity for biotin of a biotin conjugate than for free biotin, are provided along with methods of their use.

11 Claims, 4 Drawing Sheets

Specification includes a Sequence Listing.

Anti-Biotin mAb VH Variants:

```
mAb2 (IgG1):           GETVKISCKASGYTFINFGMNWVKQAPGKGLRWMGWINP-YTGEPT-YADDFKGRFAFSLETSASTAYLQ
mAb6 (IgG1):           AGGPELSCAASGFTFSSYAMSWVRQTPEKRVEWVASILS--GGYTY-YSDSMRGRFTISRDNARNILYLQ
mAb7 (IgG1            GGSLRLSCATSGFTFTDYMNWVRQPPGKALEWLGFIRNKANGYTTDYSASVKGRFTISRDNSQSILYLQ
Ref. anti-biotin       SQSLSITCTVSGFSITAYGVDWVRQPPGKGLEWLGVIWG-GGRTNY-NSGLMS-RLSIRKDNSKSQVFLT
Unrelated IgG1:        GAELVRPGTSVKVSCKAFGYAFSNYLIEWVQQRHGQGLEGIGVMIYPGSGDHKYNEKFKGKATLTADKSS (Continued)
mAb2 (IgG1):           IDNLKMEDTATYFCAR------SGWEN--PYWGQGTLVTVSAAKTTPPSV (SEQ NO: 1)
mAb6 (IgG1):           MSSLRSEDTAMYYCSRGQ--SGTYFFDYWGQGTTLTVSSAKTTPPSV (SEQ NO: 3)
mAb7 (IgG1):           MNTLRAEDSATYYCARDMRGPGTAWFAYWGQGTLVTVSAAKTTPPSV (SEQ NO: 5)
Ref. anti-biotin       MNSLQTDDTAKYYCVKHTNWDGG--FAYWGQGTTVTVSS             (SEQ NO: 13)
Unrelated IgG1:        STAYMQLSSLTSDDSAVYFCARFDYDVTYAMAYWGQGTSATV(accession #S59138.1,SEQ NO:
14)
```

FIG. 3

Anti-Biotin mAb VL Variants:

```
mAb2(kappa):        GDQASISCRSSQSLVYS-NGNTYLHWYLQKPGQSPKLLITYKVSNRFSGVPDRFSGSGSGTDFTLKIS
Unrelated kappa:    EKVTMSCKSSQSLLNSRTRKNYLAWYQQKPGQSPKLLIYWASSRESGVPDRFTGSGSGTDFTLTIS (Continued)
mAb2(kappa):        RVKAEDLGVYFCSQSTHVFWTFGGGTKLEIKRADAAPTV (SEQ ID NO:2)
Unrelated kappa:    SVQAEDLAVYYCKQSYNLY-TFGGGTKLEIK (accession #Z22039.1, SEQ ID NO:15)

mAb6(lambda):       AVVTQESALTTSPGGTVILTCRSSTGAVTTSNYANWVQEKPDHLFTGLIGGTSNRGPGVPVRFSG
mAb7(lambda):       AVVTQESALTTSPGGTVILTCRSSTGAVTTSNYANWVQEKPDHLFTGLIGGTSNRAPGVPVRFSG
Unrelated lambda:   AVVTQESALTTSPGETVTLTCRSSTGAVTISNYANWVQEKPDYLFTGLIGGTNNRAFGVPARFSG (Continued)
mAb6(lambda):       SLIGDKAALTITGAQTEDDAMYFCALWYNTHVV (SEQ ID NO:4)
mAb7(lambda):       SLIGDKAALTITGAQTEDDAMYFCALWYSTHCS (SEQ ID NO:6)
Unrelated lambda:   SLIGDKAALTITGAQTEDEAMYFCVLWYSNHWV (accession #CAC82790, SEQ ID NO:16)
```

METHODS AND COMPOSITIONS RELATING TO ANTI-BIOTIN ANTIBODIES

REFERENCE TO RELATED APPLICATION

This application claims priority to U.S. Provisional Patent Application Ser. No. 62/713,677, filed Aug. 2, 2018, the entire content of which is incorporated herein by reference.

FIELD OF THE INVENTION

Generally described are antibodies and method of use relating to detection of biotin of a biotin conjugate. Specifically described are antibodies, or antigen binding fragments thereof, which specifically bind to biotin of a biotin conjugate, and which have a higher affinity for biotin of a biotin conjugate than for free biotin.

BACKGROUND OF THE INVENTION

Increasingly, human subjects are taking biotin as a medical therapy or nutritional supplement. This practice causes difficulty in analysis of biological samples, such as blood samples, using biotin conjugate reagents since free biotin results in interference. There is a continuing need for methods and compositions for specific detection of biotin in a biotin conjugate with no or minimal interference by free biotin.

SUMMARY OF THE INVENTION

Isolated antibodies, or isolated antigen binding fragments thereof, are provided which specifically bind to biotin of a biotin conjugate, and which have a higher affinity for biotin of a biotin conjugate than for free biotin. According to aspects of the present invention, the isolated antibodies, or isolated antigen binding fragments thereof, are isolated monoclonal antibodies or isolated antigen binding fragments thereof.

Isolated antibodies, or isolated antigen binding fragments thereof, are provided which specifically bind to biotin of a biotin conjugate, which have a higher affinity for biotin of a biotin conjugate than for free biotin, and which have an attached detectable label. According to aspects of the present invention, the isolated antibodies or isolated antigen binding fragments thereof are isolated monoclonal antibodies or isolated antigen binding fragments thereof, which have an attached detectable label.

Optionally, an isolated antibody, or isolated antigen binding fragment thereof, is immobilized on a solid or semi-solid support.

Isolated antibodies, or isolated antigen binding fragments thereof, are provided which specifically bind to biotin of a biotin conjugate, which have a higher affinity for biotin of a biotin conjugate than for free biotin, and which include a heavy chain variable region 1 selected from the group consisting of: SEQ ID NO: 1, SEQ ID NO:3, and SEQ ID NO:5, or a variant of any one of SEQ ID NO: 1, SEQ ID NO:3, and SEQ ID NO:5. According to particular aspects, the variant of any one of SEQ ID NO: 1, SEQ ID NO:3, or SEQ ID NO:5 has one or more substitution mutations wherein one or more amino acids of SEQ ID NO: 1, SEQ ID NO:3, or SEQ ID NO:5 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, and which include a heavy chain variable region 1 encoded by a nucleotide sequence selected from the group consisting of: SEQ ID NO: 7, SEQ ID NO:9, SEQ ID NO:11, and a variant of any one of SEQ ID NO: 7, SEQ ID NO:9, or SEQ ID NO:11. According to particular aspects, the variant of any one of SEQ ID NO: 7, SEQ ID NO:9, or SEQ ID NO:11 encodes a heavy chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 1, SEQ ID NO:3, or SEQ ID NO:5 and which encodes one or more substitution mutations wherein one or more amino acids of the encoded heavy chain variable region 1 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, and which include a heavy chain variable region 1 encoded by a nucleotide sequence selected from the group consisting of: SEQ ID NO: 7, SEQ ID NO:9, SEQ ID NO:11, and a variant of any one of SEQ ID NO: 7, SEQ ID NO:9, or SEQ ID NO:11, wherein the variant hybridizes to the complement of SEQ ID NO: 7, SEQ ID NO:9, or SEQ ID NO:11, respectively, under stringent hybridization conditions. Such variants include those encoding one or more substitution mutations wherein one or more amino acids of the encoded heavy chain variable region 1 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, and which include a light chain variable region 1 selected from the group consisting of: SEQ ID NO: 2, SEQ ID NO:4, SEQ ID NO:6, and a variant of any one of SEQ ID NO: 2, SEQ ID NO:4, or SEQ ID NO:6. According to particular aspects, the variant of any one of SEQ ID NO: 2, SEQ ID NO:4, or SEQ ID NO:6 has one or more substitution mutations wherein one or more amino acids of SEQ ID NO: 2, SEQ ID NO:4, or SEQ ID NO:6 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, and which include a light chain variable region 1 encoded by a nucleotide sequence selected from the group consisting of: SEQ ID NO: 8, SEQ ID NO:10, SEQ ID NO:12, and a variant of any one of SEQ ID NO: 8, SEQ ID NO:10, or SEQ ID NO:12. According to particular aspects, the variant of any one of SEQ ID NO: 8, SEQ ID NO:10, or SEQ ID NO:12 encodes a light chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 2, SEQ ID NO:4, or SEQ ID NO:6 and which encodes one or more substitution mutations wherein one or more amino acids of the encoded light chain variable region 1 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, and which include a light chain variable region 1 encoded by a nucleotide sequence selected from the group consisting of: SEQ ID NO: 8, SEQ ID NO:10, SEQ ID NO:12, and a variant of any one of SEQ ID NO: 8, SEQ ID NO:10, or SEQ ID NO:12, wherein the variant hybridizes to the complement of SEQ ID NO: 8, SEQ ID NO:10, or SEQ ID NO:12, respectively, under stringent hybridization conditions. Such variants include those encoding one or more substitution mutations wherein one or more amino acids of the encoded light chain variable region 1 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, which include a heavy chain variable region 1 of SEQ ID NO:1, or a variant of SEQ ID NO:1; and which includes a light chain variable region 1 of SEQ ID NO:2, or a variant of SEQ ID NO:2. According to particular aspects, the variant of any one of SEQ ID NO:1 and/or SEQ ID NO:2 has one or more substitution mutations wherein one or more amino acids of SEQ ID NO:1 and/or SEQ ID NO:2 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, which include a heavy chain variable region 1 encoded by SEQ ID NO: 7 or a variant of SEQ ID NO: 7, and which include a light chain variable region 1 encoded by SEQ ID NO: 8 or a variant of SEQ ID NO: 8.

According to particular aspects, a variant of SEQ ID NO: 7 encodes a heavy chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 1 and which encodes one or more substitution mutations wherein one or more amino acids of the encoded heavy chain variable region 1 is replaced by a conservative amino acid substitution. According to aspects, a variant of SEQ ID NO:7 hybridizes to the complement of SEQ ID NO: 7, under stringent hybridization conditions. According to particular aspects, a variant of SEQ ID NO: 8 encodes a light chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 2 and which encodes one or more substitution mutations wherein one or more amino acids of the encoded light chain variable region 1 is replaced by a conservative amino acid substitution. According to aspects, a variant of SEQ ID NO:8 hybridizes to the complement of SEQ ID NO: 8, under stringent hybridization conditions.

Isolated antibodies, or isolated antigen binding fragments thereof, are provided which specifically bind to biotin of a biotin conjugate, which have a higher affinity for biotin of a biotin conjugate than for free biotin, and which include a heavy chain variable region 1 of SEQ ID NO: 3, or a variant of SEQ ID NO:3; which includes a light chain variable region 1 of SEQ ID NO:4, or a variant of SEQ ID NO:4. According to particular aspects, the variant of any one of SEQ ID NO:3 and/or SEQ ID NO:4 has one or more substitution mutations wherein one or more amino acids of SEQ ID NO:3 and/or SEQ ID NO:4 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, which include a heavy chain variable region 1 encoded by SEQ ID NO: 9 or a variant of SEQ ID NO: 9, and which include a light chain variable region 1 encoded by SEQ ID NO: 10 or a variant of SEQ ID NO: 10.

According to particular aspects, a variant of SEQ ID NO: 9 encodes a heavy chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 3 and which encodes one or more substitution mutations wherein one or more amino acids of the encoded heavy chain variable region 1 is replaced by a conservative amino acid substitution. According to aspects, a variant of SEQ ID NO:9 hybridizes to the complement of SEQ ID NO: 9, under stringent hybridization conditions. According to particular aspects, a variant of SEQ ID NO: 10 encodes a light chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 4 and which encodes one or more substitution mutations wherein one or more amino acids of the encoded light chain variable region 1 is replaced by a conservative amino acid substitution. According to aspects, a variant of SEQ ID NO:10 hybridizes to the complement of SEQ ID NO: 10, under stringent hybridization conditions.

Isolated antibodies, or isolated antigen binding fragments thereof, are provided which specifically bind to biotin of a biotin conjugate, which have a higher affinity for biotin of a biotin conjugate than for free biotin, which include a heavy chain variable region 1 of SEQ ID NO: 5, or a variant of SEQ ID NO:5; and which includes a light chain variable region 1 of SEQ ID NO:6, or a variant of SEQ ID NO:6. According to particular aspects, the variant of any one of SEQ ID NO:5 and/or SEQ ID NO:6 has one or more substitution mutations wherein one or more amino acids of SEQ ID NO:5 and/or SEQ ID NO:6 is replaced by a conservative amino acid substitution.

Isolated antibodies, or isolated antigen binding fragments thereof, are provided which specifically bind to biotin of a biotin conjugate, which have a higher affinity for biotin of a biotin conjugate than for free biotin, which include a heavy chain variable region 1 encoded by SEQ ID NO: 11 or a variant of SEQ ID NO: 11, and which include a light chain variable region 1 encoded by SEQ ID NO: 12 or a variant of SEQ ID NO: 12.

According to particular aspects, a variant of SEQ ID NO: 11 encodes a heavy chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 5 and which encodes one or more substitution mutations wherein one or more amino acids of the encoded heavy chain variable region 1 is replaced by a conservative amino acid substitution. According to aspects, a variant of SEQ ID NO:11 hybridizes to the complement of SEQ ID NO: 11, under stringent hybridization conditions. According to particular aspects, a variant of SEQ ID NO: 12 encodes a light chain variable region 1 of an antibody, or an antigen binding fragment thereof, which specifically binds to biotin of a biotin conjugate, which has a higher affinity for biotin of a biotin conjugate than for free biotin, which has at least 70%, at least 80%, at least 90%, or more, identity to SEQ ID NO: 6 and which encodes one or more substitution mutations wherein one or more amino acids of the encoded light chain variable region 1 is replaced by a conservative amino acid substitution. According to aspects, a variant of SEQ ID NO:12 hybridizes to the complement of SEQ ID NO: 12, under stringent hybridization conditions.

Methods for detecting a biotin conjugate in a sample are provided according to aspects of the present invention which include contacting a sample, the sample containing or suspected of containing a biotin conjugate, with an anti-biotin antibody of the present invention and/or an antigen binding fragment thereof, under binding conditions; and detecting binding of the anti-biotin antibody and/or antigen binding fragment thereof with the biotin conjugate. According to aspects, anti-biotin antibody of the present invention and/or an antigen binding fragment thereof includes SEQ ID NO:1, SEQ ID NO:2, SEQ ID NO:3, SEQ ID NO:4, SEQ ID NO:5, SEQ ID NO:6, or a variant of any thereof. According to aspects, anti-biotin antibody of the present invention and/or an antigen binding fragment thereof includes SEQ ID NO:1 and SEQ ID NO:2, or a variant of either or both thereof; SEQ ID NO:3 and SEQ ID NO:4, or a variant of either or both thereof; or SEQ ID NO:5 and SEQ ID NO:6, or a variant of either or both thereof.

According to aspects of the present invention, the method includes an ELISA.

According to aspects of the present invention, the method includes immunochromatography; antigen capture; flow cytometry; immunoblot; immunoprecipitation; immunodiffusion; competitive immunoassay, immunocytochemistry; radioimmunoassay; and combinations of any of these.

According to aspect, the sample is a human blood sample.

Immunoassay kits are provided according to aspects of the present invention which include one or more antibodies or antigen binding fragments of the present invention. According to aspects, anti-biotin antibody of the present invention and/or an antigen binding fragment thereof includes SEQ ID NO:1, SEQ ID NO:2, SEQ ID NO:3, SEQ ID NO:4, SEQ ID NO:5, SEQ ID NO:6, or a variant of any thereof. According to aspects, anti-biotin antibody of the present invention and/or an antigen binding fragment thereof includes SEQ ID NO:1 and SEQ ID NO:2, or a variant of either or both thereof; SEQ ID NO:3 and SEQ ID NO:4, or a variant of either or both thereof; or SEQ ID NO:5 and SEQ ID NO:6, or a variant of either or both thereof.

Immunoassay kits are provided according to aspects of the present invention for use in analysis of biological samples using biotin conjugate reagents and avoid interference of free biotin, such as that in blood samples from human subjects who take biotin as a medical therapy or nutritional supplement.

According to aspects, a hybridoma cell of the present invention includes a nucleic acid encoding a monoclonal antibody which specifically binds to biotin of a biotin conjugate and which has a higher affinity for biotin of a biotin conjugate than for free biotin. According to aspects, a hybridoma cell of the present invention includes one or more of: SEQ ID NO: 7 or a variant of SEQ ID NO: 7; SEQ ID NO: 8 or a variant of SEQ ID NO: 8; SEQ ID NO: 9 or a variant of SEQ ID NO: 9; SEQ ID NO: 10 or a variant of SEQ ID NO: 10; SEQ ID NO: 11 or a variant of SEQ ID NO: 11; and SEQ ID NO: 12 or a variant of SEQ ID NO: 12. According to aspects, a hybridoma cell of the present invention includes: 1) SEQ ID NO: 7 or a variant of SEQ ID NO: 7 and SEQ ID NO: 8 or a variant of SEQ ID NO: 8; 2) SEQ ID NO: 9 or a variant of SEQ ID NO: 9 and SEQ ID NO: 10 or a variant of SEQ ID NO: 10; or 3) SEQ ID NO: 11 or a variant of SEQ ID NO: 11 and SEQ ID NO: 12 or a variant of SEQ ID NO: 12.

BRIEF DESCRIPTION OF THE DRAWINGS

FIG. 3 shows an alignment of amino acid sequences of anti-biotin monoclonal antibody variable heavy (VH) chain variants: monoclonal antibody 2 (mAb2) VH chain, SEQ ID NO:1, monoclonal antibody 6 (mAb6) VH chain, SEQ ID NO:3, monoclonal antibody 7 (mAb7) VH chain, SEQ ID NO:5, a reference anti-biotin VH chain, SEQ ID NO:13, a VH chain of an unrelated IgG1 antibody, SEQ ID NO:14, and shows percent of the aligned residues (including deletions and insertions) which are different from the indicated reference sequences: mAb2 VH: 58.9% ($^{66}/_{112}$); mAb6 VH: 53.6% ($^{60}/_{112}$); mAb7 VH: 50.0% ($^{56}/_{112}$);

FIG. 4 shows an alignment of amino acid sequences of anti-biotin monoclonal antibody variable light (VL) chain variants: monoclonal antibody 2 (mAb2) VL kappa chain, SEQ ID NO:2, monoclonal antibody 6 (mAb6) VL lambda chain, SEQ ID NO:4, monoclonal antibody 7 (mAb7) VL lambda chain, SEQ ID NO:6, a kappa VL chain of an unrelated mouse antibody (accession #Z22039.1), SEQ ID NO:15, and a lambda VL chain of an unrelated mouse antibody, SEQ ID NO:16 (accession #CAC82790), and shows percent of the aligned residues (including deletions and insertions) which are different from the indicated reference sequences: mAb2 VL: 33.0% ($^{32}/_{97}$); mAb6 VL: 10.2% ($^{10}/_{98}$); mAb7 VL: 9.2% ($^{9}/_{98}$).

DETAILED DESCRIPTION OF THE INVENTION

Figure 1:
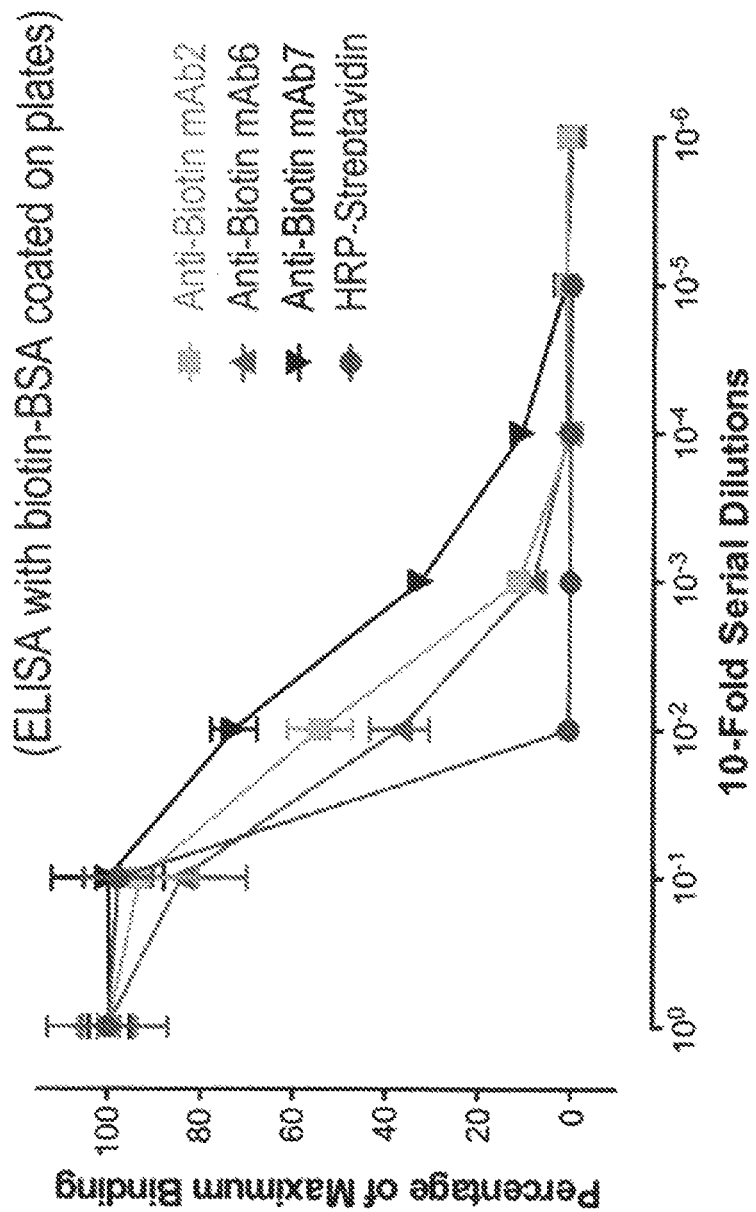
FIG. 1 is a graph showing that anti-biotin monoclonal antibodies of the present invention have affinities to biotin-BSA conjugate similar to that of streptavidin.
Figure 2:
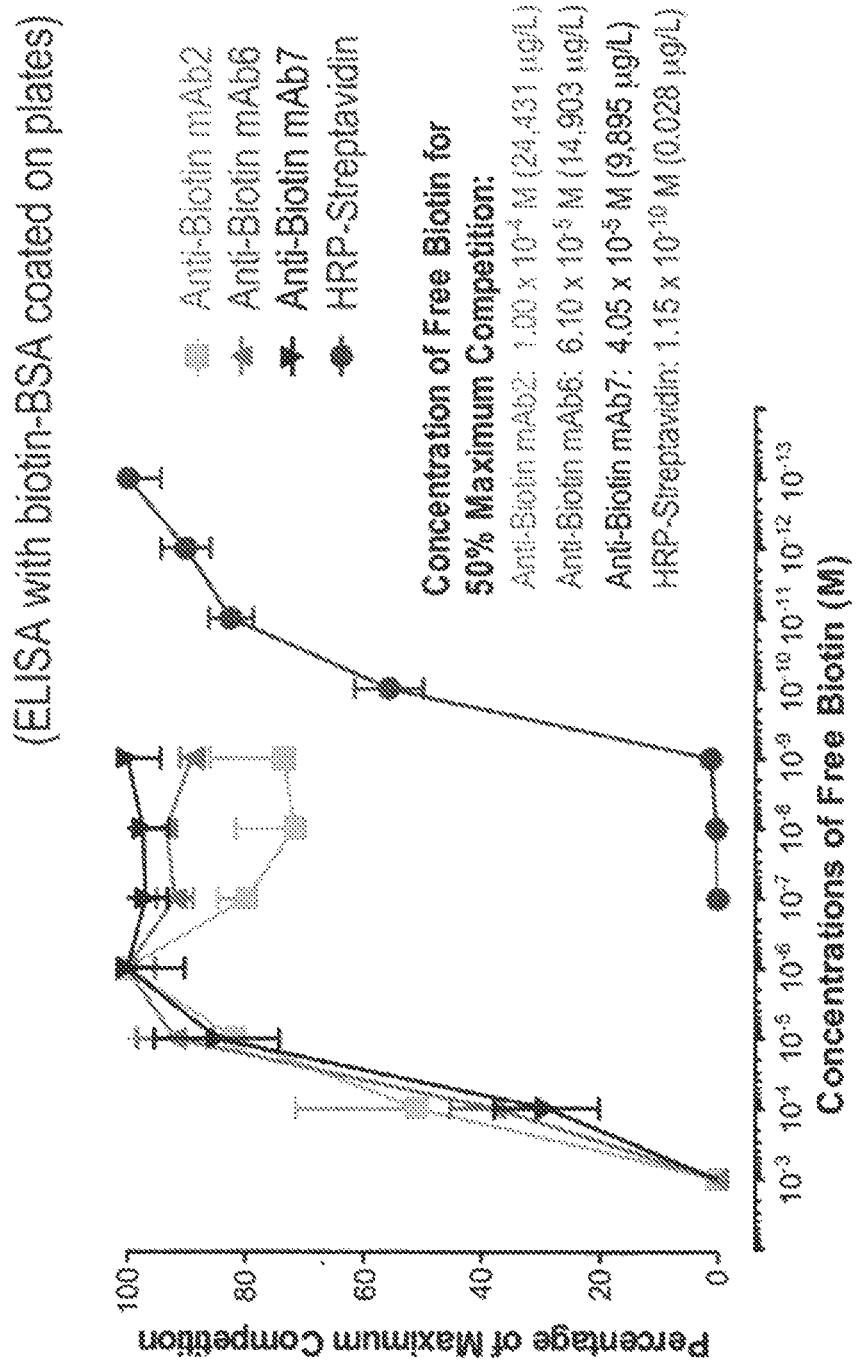
FIG. 2 is a graph showing that anti-biotin monoclonal antibodies of the present invention have 350,000-870,000-fold lower affinities to free biotin than that of streptavidin.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Engelke, D. R., RNA Interference (RNAi): Nuts and Bolts of RNAi Technology, DNA Press LLC, Eagleville, P A, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808; Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

The singular terms "a," "an," and "the" are not intended to be limiting and include plural referents unless explicitly stated otherwise or the context clearly indicates otherwise.

Antibodies

Antibodies which specifically bind to the biotin of biotin conjugates with high affinity and do not bind to free biotin or bind to free biotin only with much lower affinity to free biotin, are provided according to aspects of the present invention. The terms "anti-biotin antibody" and "anti-biotin mouse monoclonal antibody" (abbreviated as anti-biotin mAb or anti-biotin mouse mAb), as used herein to refer to antibodies of the present invention, refers to antibodies which specifically bind to the biotin of biotin conjugates with high affinity and which do not bind to free biotin or bind to free biotin only with much lower affinity.

The term "biotin conjugate" refers to biotin covalently bonded to any material, typically, but not limited to, an organic material, illustratively including a protein, a protein fragment, a peptide, a carbohydrate, a nucleic acid, an oligonucleotide, a lipid, a magnetic particle, a polymer, or an oligomer. Biotin conjugates include biotin conjugated to a member of a binding pair, illustratively including any of: an antibody, antigen binding fragment, antigen, aptamer, lectin, carbohydrate, ligand, receptor, a chemical, a fluorophore, or a pharmacological compound.

As used herein, the terms "antibody" and "antibodies" relate to monoclonal antibodies, polyclonal, bispecific antibodies, multispecific antibodies, chimeric antibodies, camelized antibodies, single domain antibodies, single-chain Fvs (scFv), single chain antibodies, disulfide-linked Fvs (sdFv), and antigen-binding fragments of any of these. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class or subclass (e.g., IgG1, IgG2 including IgG2a and IgG2b, IgG3, IgG4, IgA1 and IgA2).

As used herein, the term "antigen-binding fragment" defines a fragment of an antibody that immunospecifically binds to a target antigen. An antigen-binding fragment may be generated by any technique known to one of skill in the art. For example, Fab and F(ab')2 antigen-binding fragments may be produced by proteolytic cleavage of immunoglobulin molecules, using enzymes such as papain (to produce Fab antigen-binding fragments) or pepsin (to produce F(ab')2 antigen-binding fragments). Antigen-binding fragments are also produced by recombinant DNA technologies. Antigen-binding fragments encompassed by the present compositions and methods possess the ability to specifically bind biotin when the biotin is present in a biotin conjugate.

Antibodies, antigen-binding fragments and methods for their generation are known in the art, for instance, as described in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

Generally described, antibodies contain heavy chain polypeptides and light chain polypeptides. Antigen recognition is mediated by variable regions of the heavy and light chains. Complementarity determining region (CDR) refers to polypeptide regions within the variable region of heavy and light chains. Three CDRs (CDR1, CDR2 and CDR3) are present in each light chain variable region ($V_L$) and each heavy chain variable region ($V_H$). The CDRs are generally responsible for specific antigen recognition properties of the antibody or antigen-binding fragment.

Antibodies according to aspects of the present invention are mouse monoclonal anti-biotin antibodies which specifically bind to the biotin of biotin conjugates with high affinity and do not bind to free biotin or bind to free biotin only with much lower affinity to free biotin. Three representative anti-biotin mouse mAbs are provided according to aspects of the present invention: mAb2, mAb6, and mAb7.

All of mAb2, mAb6, and mAb7 specifically bind to the biotin of biotin conjugates with high affinity and do not bind to free biotin or bind to free biotin only with much lower affinity to free biotin.

Hybridoma cells which produce mAb2, mAb6, and mAb7 are provided according to aspects of the present invention, including hybridoma 2 which expresses mouse monoclonal antibody mAb2; hybridoma 6 which expresses mouse monoclonal antibody mAb6; and hybridoma 7 which expresses mouse monoclonal antibody mAb7.

Antibodies and antigen binding fragments according to aspects of the present invention are "isolated." The term "isolated" in the context of an antibody or antigen binding fragment refers to separation of the antibody or antigen binding fragment from at least one other component present in the system in which the antibody was produced. For example, monoclonal antibodies are separated from hybridoma cells, or the culture media, or body fluid in which they are produced, generating isolated monoclonal antibodies.

According to aspects, antibodies and antigen binding fragments are substantially purified to produce an isolated antibody or antigen binding fragment. The term "substantially purified" refers to antibodies and antigen binding fragments separated from other substances, such as those naturally present in a hybridoma cell, culture media, body fluid or chemical synthesis reaction, so that the antibodies and antigen binding fragments make up at least about 0.01-100% of the mass, by weight, such as about 0.01%, 0.1%, 1%, 5%, 10%, 25%, 50% 75% or greater than about 75% of the mass, by weight, of the isolated antibodies and antigen binding fragments.

Such purification is achieved by techniques illustratively including salt, pH, hydrophobic or affinity precipitation, electrophoretic methods such as gel electrophoresis and 2-D gel electrophoresis; chromatography methods such as HPLC, ion exchange chromatography, affinity chromatography, size exclusion chromatography, thin layer and paper chromatography.

Substitution at one or more amino acids in a CDR is possible while retaining specific antigen-binding function, particularly for those amino acid residues that do not contact the antigen. Such substitutions may be made at positions identified and known in the art or may be made empirically.

mAb2 mAb2 is characterized by heavy chain variable region 1 (VH1, SEQ ID NO: 1) and light chain variable region 1 (VL1, SEQ ID NO: 2).

According to aspects of the present invention, a monoclonal antibody or an antigen-binding fragment thereof which is characterized by specific binding to biotin in a biotin conjugate includes a heavy chain variable region including the amino acid sequence SEQ ID NO: 1, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 1, and retains at least a substantial proportion (at least about 50%, 60%, 70%, 80%, 90%, 95%, 98%, 99% or more) of the affinity/avidity and/or the specificity/selectivity of the parent antibody mAb2, and in some cases such an antibody may be associated with greater affinity, selectivity and/or specificity than the parent antibody mAb2.

SEQ ID NO: 1 Monoclonal Antibody mAb2 IgG1 Variable Heavy Chain Region (110 Amino Acids)

GETVKISCKASGYTFINFGMNWVKQAPGKGLKWMGWINPYTGEPTYADD

FKGRFAFSLETSASTAYLQIDNLKNEDTATYFCARSGWENPYWGQGTLV

TVSAAKTTPPSV

According to aspects of the present invention, a monoclonal antibody or an antigen-binding fragment thereof which is characterized by specific binding to biotin in a biotin conjugate includes a light chain variable region including the amino acid sequence SEQ ID NO: 2, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 2, and retains at least a substantial proportion (at least about 50%, 60%, 70%, 80%, 90%, 95%, 98%, 99% or more) of the affinity/avidity and/or the specificity/selectivity of the parent antibody mAb2, and in some cases such an antibody may be associated with greater affinity, selectivity and/or specificity than the parent antibody mAb2.

SEQ ID NO: 2 Monoclonal Antibody mAb2 Kappa Variable Light Chain Region (105 Amino Acids)

GDQASISCRSSQRLVYSNGNTYLHWYLQKPGQSPKLLIYKVSNRFSGVP

DRFSGSGSGTDFTLKISRVKAEDLGVYFCSQSTHVPWTFGGGTKLEIKR

ADAAPTV mAb6 mAb6 is characterized by heavy chain variable region 1 (VH1, SEQ ID NO: 3) and light chain variable region 1 (VL1, SEQ ID NO: 4).

According to aspects of the present invention, a monoclonal antibody or an antigen-binding fragment thereof which is characterized by specific binding to biotin in a biotin conjugate includes a heavy chain variable region including the amino acid sequence SEQ ID NO: 3, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 3, and retains at least a substantial proportion (at least about 50%, 60%, 70%, 80%, 90%, 95%, 98%, 99% or more) of the affinity/avidity and/or the specificity/selectivity of the parent antibody mAb6, and in some cases such an antibody may be associated with greater affinity, selectivity and/or specificity than the parent antibody mAb6.

SEQ ID NO: 3 Monoclonal Antibody mAb6 IgG1 Variable Heavy Chain Region (112 Amino Acids)

AGGPELSCAASGFTFSSYAMSWVRQTPEKRVEWVASILSGGYIYYSDSM

RGRFTISRDNARNILYLQMSSLRSEDTAMYYCSRGQSGTVFFDYWGQGT

TLTVSSAKTTPPSV

According to aspects of the present invention, a monoclonal antibody or an antigen-binding fragment thereof which is characterized by specific binding to biotin in a biotin conjugate includes a light chain variable region including the amino acid sequence SEQ ID NO: 4, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 4, and retains at least a substantial proportion (at least about 50%, 60%, 70%, 80%, 90%, 95%, 98%, 99% or more) of the affinity/avidity and/or the specificity/selectivity of the parent antibody mAb6, and in some cases such an antibody may be associated with greater affinity, selectivity and/or specificity than the parent antibody mAb6.

SEQ ID NO: 4 Monoclonal Antibody mAb6 Lambda Variable Light Chain Region (98 Amino Acids)

AVVTQESALTTSPGGTVILTCRSSTGAVTTSNYANWVQEKPDHLFTGLI

GGTSNRGPGVPVRFSGSLIGDKAALTITGAQTEDDAMYFCALWYNTHYV mAb7 mAb7 is characterized by heavy chain variable region 1 (VH1, SEQ ID NO: 5) and light chain variable region 1 (VL1, SEQ ID NO: 6).

According to aspects of the present invention, a monoclonal antibody or an antigen-binding fragment thereof which is characterized by specific binding to biotin in a biotin conjugate includes a heavy chain variable region including the amino acid sequence SEQ ID NO: 5, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 5, and retains at least a substantial proportion (at least about 50%, 60%, 70%, 80%, 90%, 95%, 98%, 99% or more) of the affinity/avidity and/or the specificity/selectivity of the parent antibody mAb7, and in some cases such an antibody may be associated with greater affinity, selectivity and/or specificity than the parent antibody mAb7.

SEQ ID NO: 5 Monoclonal Antibody mAb7 IgG1 Variable Heavy Chain Region (117 Amino Acids)

GGSLRLSCATSGFTFTDYYMNWVRQPPGKALEWLGFIRNKANGYTTDYS

ASVKGRFTISRDNSQSILYLQMNTLRAEDSATYYCARDMRGPGTAWFAY

WGQGTLVTVSAAKTTPPSV

According to aspects of the present invention, a monoclonal antibody or an antigen-binding fragment thereof which is characterized by specific binding to biotin in a biotin conjugate includes a light chain variable region including the amino acid sequence SEQ ID NO: 6, or a variant thereof. The variant includes an amino acid sequence having at least 70%, at least 75%, at least 80%, at least 85%, at least 90%, at least 95%, at least 96%, at least 97%, at least 98%, at least 99%, or greater than 99%, identity with the amino acid sequence of SEQ ID NO: 6, and retains at least a substantial proportion (at least about 50%, 60%, 70%, 80%, 90%, 95%, 98%, 99% or more) of the affinity/avidity and/or the specificity/selectivity of the parent antibody mAb7, and in some cases such an antibody may be associated with greater affinity, selectivity and/or specificity than the parent antibody mAb7.

SEQ ID NO: 6 Monoclonal Antibody mAb7 Lambda Variable Light Chain Region (98 Amino Acids)

AVVTQESALTTSPGGTVILTCRSSTGAVTTSNYANWVQEKPDHLFTGLI

GGTSNRAPGVPVRFSGSLIGDKAALTITGAQTEDDAMYFCALWYSTHCS

The phrase "specific binding" and grammatical equivalents as used herein in reference to binding of an anti-biotin antibody or anti-biotin antigen binding fragment, refers to binding of the antibody or antigen binding fragment to biotin in a biotin conjugate without substantial binding to substances other than biotin present in a biotin conjugate. It is understood by the ordinarily skilled artisan that specific binding refers to specific binding as determinable by use of appropriate controls to distinguish it from nonspecific binding.

According to aspects of the present invention, the phrase "specific binding" and grammatical equivalents as used herein in reference to binding of an anti-biotin antibody or anti-biotin antigen binding fragment to biotin, when the biotin is present in a biotin conjugate, without substantial binding to other substances, particularly free biotin. An anti-biotin antibody or anti-biotin antigen binding fragment according to aspects of the present invention specifically binds to biotin of a biotin conjugate when the antibody or antigen binding fragment has an affinity constant (KA) greater than $1 \times 10^6$ M for biotin of the biotin conjugate, and an affinity constant lower than $1 \times 10^4$ M for free biotin. The term "without substantial binding to other substances" refers to a minimal amount of binding to related substances, such as free biotin, when free biotin and conjugated biotin are present together in a sample.

Methods and compositions of the present invention are not limited to particular amino acid sequences identified herein and variants of a reference peptide or protein are encompassed.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length. Optionally, the two sequences are natural variants of a structural domain of a protein or two related proteins.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleotide or amino acid mutations can be introduced without altering the functional properties of a given nucleic acid or protein, respectively. Mutations can be introduced using standard molecular biology techniques, such as site-directed mutagenesis and PCR-mediated mutagenesis, to produce variants. For example, one or more amino acid substitutions, additions, or deletions can be made without altering the functional properties of a reference protein.

When comparing a reference protein to a putative variant, amino acid similarity may be considered in addition to identity of amino acids at corresponding positions in an amino acid sequence. "Amino acid similarity" refers to amino acid identity and conservative amino acid substitutions in a putative variant compared to the corresponding amino acid positions in a reference protein.

Conservative amino acid substitutions can be made or may be present in reference proteins to produce or identify variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar/nonpolar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size; alanine, cysteine, aspartate, glycine, asparagine, proline, threonine, serine, valine are all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

According to aspects of the present invention, a monoclonal antibody or an antigen-binding fragment thereof which is characterized by specific binding to biotin of a biotin conjugate includes a variable heavy chain region, or a variant thereof, encoded by the nucleotide sequence of SEQ ID NO: 7 or a variant of SEQ ID NO: 7 which hybridizes to the complement of SEQ ID NO: 7 under stringent hybridization conditions.

SEQ ID NO: 7 Monoclonal Antibody mAb2 IgG1 Variable Heavy Chain Region (335 Nucleotides)

AGTCAAGATCTCCTGCAAGGCTTCTGGATATACCTTCATAAACTTTGGA

ATGAACTGGGTGAAGCAGGCTCCAGGAAAGGGTTTAAAGTGGATGGGCT

GGATAAACCCCTACACTGGAGAACCAACATATGCGGATGACTTCAAGGG

ACGGTTTGCCTTCTCTTTGGAAACCTCTGCCAGCACTGCCTATTTGCAG

ATCGACAACCTCAAAAATGAGGACACGGCTACATATTTCTGTGTGCAAGAT

CCGGGTGGGAAAACCCTTACTGGGGCCAAGGGACTCTGGTCACTGTCTC

TGCAGCCAAAACGACACCCCCATCTGTCTATAGATCTTCCA

According to aspects of the present invention, a monoclonal antibody or an antigen-binding fragment thereof which is characterized by specific binding to biotin of a biotin conjugate includes a variable light chain region, or a variant thereof, encoded by the nucleotide sequence of SEQ ID NO: 8 or a variant of SEQ ID NO: 8 which hybridizes to the complement of SEQ ID NO: 8 under stringent hybridization conditions.

SEQ ID NO: 8 Monoclonal Antibody mAb2 Kappa Variable Light Chain Region (282 Nucleotides)

AGACTTGTATACAGTAATGGAAACACCTATTTACATTGGTACCTGCAGA

AGCCAGGCCAGTCTCCAAAACTCCTGATCTACAAAGTTTCCAACCGATT

TTCTGGGGTCCCAGACAGGTTCAGTGGCAGTGGATCAGGGACAGATTTC

ACACTCAAGATCAGCAGAGTGAAGGCTGAGGATCTGGGAGTTTATTTCT

GCTCTCAAAGTACACATGTTCCGTGGACGTTCGGTGGAGGCACCAAGCT

GGAAATCAAACGGGCTGATGCTGCACCAACTGTATCC

According to aspects of the present invention, a monoclonal antibody or an antigen-binding fragment thereof which is characterized by specific binding to biotin of a biotin conjugate includes: 1) a variable heavy chain region, or a variant thereof, encoded by the nucleotide sequence of SEQ ID NO: 7 or a variant of SEQ ID NO: 7 which hybridizes to the complement of SEQ ID NO: 7 under stringent hybridization conditions and 2) a variable light chain region, or a variant thereof, encoded by the nucleotide sequence of SEQ ID NO: 8 or a variant of SEQ ID NO: 8 which hybridizes to the complement of SEQ ID NO: 8 under stringent hybridization conditions.

According to aspects of the present invention, a monoclonal antibody or an antigen-binding fragment thereof which is characterized by specific binding to biotin of a biotin conjugate includes a variable heavy chain region, or a variant thereof, encoded by the nucleotide sequence of SEQ ID NO: 9 or a variant of SEQ ID NO: 9 which hybridizes to the complement of SEQ ID NO: 9 under stringent hybridization conditions.

SEQ ID NO: 9 Monoclonal Antibody mAb6 IgG1 Variable Heavy Chain Region (325 Nucleotides)

GAACTCTCCTGTGCAGCCTCTGGATTCACTTTCAGTAGTTATGCCATGT

CTTGGGTTCGCCAGACTCCAGAGAAGAGGGTGGAGTGGGTCGCATCCAT

TCTTAGTGGTGGTTATATTTATTATTCAGACAGTATGAGGGGTCGATTC

ACCATCTCCAGAGATAATGCCAGGAACATCCTGTACCTGCAAATGAGCA

GTCTGAGGTCTGAGGACACGGCCATGTATTACTGTTCAAGAGGCCAAAG

TGGGACGGTTTTTTTTGACTACTGGGGCCAAGGCACCACTCTCACAGTC

TCCTCAGCCAAAACGACACCCCCATCTGTCT

According to aspects of the present invention, a monoclonal antibody or an antigen-binding fragment thereof which is characterized by specific binding to biotin of a biotin conjugate includes a variable light chain region, or a variant thereof, encoded by the nucleotide sequence of SEQ ID NO: 10 or a variant of SEQ ID NO: 10 which hybridizes to the complement of SEQ ID NO: 10 under stringent hybridization conditions.

SEQ ID NO: 10 Monoclonal Antibody mAb6 Lambda Variable Light Chain Region (310 Nucleotides)

GCCGAACATAATGGGTGTTGTACCATAGAGCACAGAAATACATTGCATC

ATCCTCAGTCTGTGCCCCTGTGATGGTGAGGGCAGCCTTGTCTCCAATC

AGGGAGCCTGAGAATCTGACAGGAACACCTGGACCTCGGTTGCTGGTAC

CACCTATTAGACCAGTGAATAAATGATCTGGTTTTTCTTGGACCCAGTT

GGCATAGTTACTAGTTGTAACAGCCCCAGTACTTGAGCGACAAGTGAGT

ATGACTGTTCCACCAGGTGATGTGGTGAGTGCAGATTCCTGAGTCACAA

CAGCCTGGCATGCACC

According to aspects of the present invention, a monoclonal antibody or an antigen-binding fragment thereof which is characterized by specific binding to biotin of a biotin conjugate includes: 1) a variable heavy chain region, or a variant thereof, encoded by the nucleotide sequence of SEQ ID NO: 9 or a variant of SEQ ID NO: 9 which hybridizes to the complement of SEQ ID NO: 9 under stringent hybridization conditions and 2) a variable light chain region, or a variant thereof, encoded by the nucleotide sequence of SEQ ID NO: 10 or a variant of SEQ ID NO: 10 which hybridizes to the complement of SEQ ID NO: 10 under stringent hybridization conditions.

According to aspects of the present invention, a monoclonal antibody or an antigen-binding fragment thereof which is characterized by specific binding to biotin of a biotin conjugate includes a variable heavy chain region, or a variant thereof, encoded by the nucleotide sequence of SEQ ID NO: 11 or a variant of SEQ ID NO: 11 which hybridizes to the complement of SEQ ID NO: 11 under stringent hybridization conditions.

SEQ ID NO: 11 Monoclonal Antibody mAb7 IgG1 Variable Heavy Chain Region (349 Nucleotides)

GGGGGTTCTCTGAGACTCTCCTGTGCAACTTCTGGGTTCACCTTCACTG

ATTACTACATGAACTGGGTCCGCCAGCCTCCAGGAAAGGCACTTGAGTG

GTTGGGTTTTATTAGAAACAAAGCAAATGGTTACACAACAGACTACAGT

GCATCTGTGAAGGGTCGGTTCACCATCTCCAGAGATAATTCCCAAAGCA

TCCTCTATCTTCAAATGAATACCCTGCGAGCTGAAGACAGTGCCACTTA

TTACTGTGCAAGAGATATGAGGGGGCCTGGGACGGCCTGGTTTGCTTAC

TGGGGCCAAGGGACTCTGGTCACTGTCTCTGCAGCCAAAACGACACCCC

CATCTG

According to aspects of the present invention, a monoclonal antibody or an antigen-binding fragment thereof which is characterized by specific binding to biotin of a biotin conjugate includes a variable light chain region, or a variant thereof, encoded by the nucleotide sequence of SEQ ID NO: 12 or a variant of SEQ ID NO: 12 which hybridizes to the complement of SEQ ID NO: 12 under stringent hybridization conditions.

SEQ ID NO: 12 Monoclonal Antibody mAb7 Lambda Variable Light Chain Region (290 Nucleotides)

CAATGGGTGCTGTACCATAGAGCACAGAAATACATTGCATCATCCTCAG

TCTGTGCCCCTGTGATGGTGAGGGCAGCCTTGTCTCCAATCAGGGAGCC

TGAGAATCTGACAGGAACACCTGGAGCTCGGTTGCTGGTACCACCTATT

AGACCAGTGAATAAATGATCTGGTTTTTCTTGGACCCAGTTGGCATAGT

TACTAGTTGTAACAGCCCCAGTACTTGAGCGACAAGTGAGTATGACTGT

TCCACCAGGTGATGTGGTGAGTGCAGATTCCTGAGTCACAACAGC

According to aspects of the present invention, a monoclonal antibody or an antigen-binding fragment thereof which is characterized by specific binding to biotin of a biotin conjugate includes: 1) a variable heavy chain region, or a variant thereof, encoded by the nucleotide sequence of SEQ ID NO: 11 or a variant of SEQ ID NO: 11 which hybridizes to the complement of SEQ ID NO: 11 under stringent hybridization conditions and 2) a variable light chain region, or a variant thereof, encoded by the nucleotide sequence of SEQ ID NO: 12 or a variant of SEQ ID NO: 12 which hybridizes to the complement of SEQ ID NO: 12 under stringent hybridization conditions.

It will be appreciated by those of ordinary skill in the art that, due to the degenerate nature of the genetic code, alternate nucleic acid sequences encode the variable heavy chain regions, variable light chain regions and variants thereof disclosed herein and that such alternate nucleic acids may be used in compositions and methods described herein.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002. A non-limiting example of high stringency hybridization conditions includes hybridization in 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes.

Immunoassays

Detection of a biotin conjugate in a biological sample according to aspects of the present invention is accomplished by immunoassay using an antibody or antigen binding fragment thereof which specifically binds biotin in a biotin conjugate.

Methods of detection of biotin of a biotin conjugate in a sample according to aspects of the present invention include contacting a sample containing or suspected of containing a biotin conjugate under antigen/antibody binding conditions with a detectably labeled anti-biotin antibody of the present invention, or biotin conjugate (in a competitive assay format), wherein the detectable label is directly or indirectly attached to the anti-biotin antibody. If present, the biotin conjugate binds to the detectably labeled anti-biotin antibody to form a complex such that specific detection of the complex is indicative of the biotin conjugate in the sample. Advantageously, the anti-biotin antibody has little or no affinity to free biotin such that any free biotin in the sample does not interfere with specific detection of the biotin conjugate.

The term "detectable label" refers to any atom or moiety that can provide a detectable signal and which can be attached to a binding agent, such as a primary or secondary antibody or antigen binding fragment, or analyte. Examples of such detectable labels include fluorescent moieties, chemiluminescent moieties, bioluminescent moieties, ligands, particles, latex particles, luminescent particles, magnetic particles, fluorescent particles, colloidal gold, enzymes, enzyme substrates, radioisotopes and chromophores. Such particles can be of any shape, size, composition, or physiochemical characteristics compatible with assay conditions. The particles can be microparticles having a diameter of less than one millimeter, for example, a size ranging from about 0.1 to about 1,000 micrometers in diameter, inclusive, such as about 3-25 microns in diameter, inclusive, or about 5-10 microns in diameter, inclusive. The particles can be nanoparticles having a diameter from about 1 nanometer (nm) to about 100,000 nm in diameter, inclusive, for example, a size ranging from about 10-1,000 nm, inclusive, or for example, a size ranging from 200-500 nm, inclusive.

Any appropriate method, including but not limited to spectroscopic, optical, photochemical, biochemical, enzymatic, electrical, isotopic, magnetic, energetic, immunochemical and/or via nucleotide amplification such as using PCR is used to detect a detectable label in an assay described herein.

Immunoassays are well-known in the art and include, but are not limited to, enzyme-linked immunosorbent assay (ELISA) such as but not limited to, antigen capture ELISA, indirect ELISA, competitive ELISA, fixed cell ELISA; immunochromatography; antigen capture; flow cytometry; immunoblot; immunoprecipitation; immunodiffusion; competitive immunoassays, immunocytochemistry; radioimmunoassay; and combinations of any of these. Generalized details of immunoassays are described in standard references, illustratively including Wild, D., The Immunoassay Handbook, 3rd Ed., Elsevier Science, 2005; Gosling, J. P., Imunoassays: A Practical Approach, Practical Approach Series, Oxford University Press, 2005; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Ormerod, M. G., Flow Cytometry: a practical approach, Oxford University Press, 2000; and Givan, A. L., Flow Cytometry: first principles, Wiley, New York, 2001.

Immunoassay according to aspects of the present invention may include contacting an anti-biotin antibody or antigen binding fragment thereof with a sample, wherein the anti-biotin antibody or antigen binding fragment thereof, is immobilized on a solid support to detect binding of the anti-biotin antibody or antigen binding fragment thereof with biotin of a biotin conjugate in the biological sample.

Immunoassay using an anti-biotin antibody that has significantly higher affinity to biotin of a biotin conjugate than that to free biotin according to aspects of the present invention can avoid interference of free biotin in biological samples such as blood samples from human subjects who take biotin as a medical therapy or nutritional supplement. This advantage over avidin or streptavidin that has higher affinity to free biotin than biotin of a biotin conjugate makes anti-biotin antibody according to aspects of the present invention a solution for interference of free biotin in blood samples of human subjects who take biotin as a medical therapy or nutritional supplement, an increasing problem for all avidin or streptavidin-based assay methods used in medical diagnosis and other related applications.

Optionally an immunoassay according to aspects of the present invention is performed using a competitive immunoassay format including immobilization of a biotin conjugate.

Using an anti-biotin antibody that has significantly higher affinity to biotin of a biotin conjugate than that to free biotin according to aspects of the present invention, a competitive immunoassay can detect biotin conjugates with enhanced sensitivity when using free biotin labeled with radioactive or non-radioactive isotope or small molecule such as, not limited to, a fluorescent dye, as indicator, because of biotin conjugate's higher affinity to compete for the anti-biotin antibody.

The term "solid support" as used herein includes both solid supports and semi-solid supports. The term "solid porous support" as used herein includes both solid porous supports and semi-solid porous supports. The solid support can be in any of various forms or shapes, including planar, such as but not limited to membranes, silicon chips, glass plates and dipsticks; or three dimensional such as but not limited to particles, microtiter plates, microtiter wells, pins and fibers.

A solid support for attachment of an antibody or antigen binding fragment can be any of various materials such as glass; plastic, such as polypropylene, polystyrene, nylon; paper; silicon; nitrocellulose; or any other material to which the antibody, antigen binding fragment or antigen can be attached for use in an assay.

In particular aspects, a solid support to which an antibody, antigen binding fragment, or antigen is attached is a particle which is stable and insoluble under assay conditions. The particles can be of any shape, size, composition, or physiochemical characteristics compatible with assay conditions. The particle characteristics are optionally chosen so that the particle can be separated from fluid, e.g., on a filter with a particular pore size or by some other physical property, e.g., a magnetic property.

The particles are optionally latex particles, luminescent particles, magnetic particles, or fluorescent particles.

The particles can be of any shape, size, composition, or physiochemical characteristics compatible with assay conditions. The particles can be microparticles having a diameter of less than one millimeter, for example, a size ranging from about 0.1 to about 1,000 micrometers in diameter, inclusive, such as about 3-25 microns in diameter, inclusive, or about 5-10 microns in diameter, inclusive. The particles can be nanoparticles having a diameter from about 1 nanometer (nm) to about 100,000 nm in diameter, inclusive, for example, a size ranging from about 10-1,000 nm, inclusive, or for example, a size ranging from 200-500 nm, inclusive. The particles are can be organic or inorganic particles, such as glass or metal and can be particles of a synthetic or naturally occurring polymer, such as polystyrene, polycarbonate, silicon, nylon, cellulose, agarose, dextran, and polyacrylamide. Particles are latex beads according to aspects of the present invention.

Particles used are optionally encoded and distinguishable from other particles based on a characteristic such as color, reflective index and/or an imprinted or otherwise optically detectable pattern. For example, the particles may be encoded using optical, chemical, physical, or electronic tags. Encoded particles can contain or be attached to, one or more fluorophores which are distinguishable, for instance, by excitation and/or emission wavelength, emission intensity, excited state lifetime or a combination of these or other optical characteristics. Optical bar codes can be used to encode particles.

A solid support can be in the form of a lateral flow strip used in immunochromatography assay (ICA), i.e., a lateral flow test.

One or more washing steps is optionally included in an immunoassay according to aspects of the present invention, to remove unwanted and/or unbound materials.

Any reaction or diluent buffer compatible with the sample, reagents and reaction can be used in immunoassays, such as for dilution and/or washing steps, including but not limited to phosphate buffered saline, sodium phosphate buffer, potassium phosphate buffer, Tris-HCl buffer, Tricine buffer and other buffers described herein.

The sample may be diluted or processed to purify or concentrate a biotin conjugate or biotin conjugates prior to analysis. A biotin conjugate contained in a sample is optionally purified or concentrated for assay according to a method of the present invention.

The term "purified" in the context of a biological sample refers to separation of a biotin conjugate in the sample from at least one other component present in the biological sample.

According to aspects, a biotin conjugate is substantially purified from the biological sample to produce a substantially purified sample for use in an inventive assay. The term "substantially purified" refers to a desired material separated from other substances naturally present in a sample obtained from the subject so that the desired material makes up at least about 0.01-100% of the mass, by weight, such as about 0.01%, 0.1%, 1%, 5%, 10%, 25%, 50% 75% or greater than about 75% of the mass, by weight, of the substantially purified sample.

Sample purification is achieved by techniques illustratively including salt, pH, hydrophobic or affinity precipitation, electrophoretic methods such as gel electrophoresis and 2-D gel electrophoresis; chromatography methods such as HPLC, ion exchange chromatography, affinity chromatography, size exclusion chromatography, thin layer and paper chromatography. It is appreciated that electrophoresis and chromatographic methods can also be used to separate a peptide or peptides from other components in a sample in the course of performing an assay, as in, for example separation of proteins in immunoblot assays.

According to one aspect of the present invention, a biotin conjugate is isolated and concentrated by absorption onto a solid substrate.

According to aspects of the present invention, immunoassay includes assay of a biotin conjugate in a sample by an ELISA technique.

Optionally, a control or standard is included in an assay according to aspects of the present invention.

The terms "control" and "standard" are familiar to those of ordinary skill in the art and refer to any control or standard that can be used for comparison. The control or standard may be determined prior to assay for biotin in a biotin conjugate, in parallel, simultaneously, in a multiplex assay or other assay format. A control or standard can be a negative control and/or a positive control.

A sample which is assayed for a biotin conjugate according to methods of the invention may be any sample containing or suspected of containing the biotin conjugate including, an aqueous buffer, a mammalian cell culture medium, a bacterial culture medium, cell or bacterial extract, whole blood, plasma, serum, urine, saliva and other human or animal body fluids.

According to aspects, immunoassay kits for detecting the biotin of biotin conjugates in a biological sample are provided which include one or more antibodies or antigen binding fragments which specifically bind to the biotin of biotin conjugates.

According to aspects, immunoassay kits for detecting the biotin of biotin conjugates in a biological sample are provided which include one or more antibodies or antigen binding fragments selected from: mAb2, mAb6, mAb7, an antigen binding fragment which specifically binds to the biotin of biotin conjugates, or a variant of any thereof which specifically binds to the biotin of biotin conjugates.

One or more auxiliary components are optionally included in such kits, such as a control such as one or more biotin conjugates, a secondary antibody, one or more reaction vessels, a buffer, diluent or a reconstituting agent.

Embodiments of inventive compositions and methods are illustrated in the following examples. These examples are provided for illustrative purposes and are not considered limitations on the scope of inventive compositions and methods.

EXAMPLES

Monoclonal Antibody Development:

8-week-old female Balb/c mice were immunized with biotin-KLH conjugate. Spleen cells were harvested from the immunized mouse to fuse with SP2/0-Ag14 mouse myeloma cells. Hybridomas were selected by HAT (0.1 mM hypoxanthine, 0.4 µM aminopterin, 16 µM thymidine) media and screened with indirect ELISA against immobilized biotin-BSA conjugate using horseradish peroxidase (HRP)-labeled, goat anti-mouse total immunoglobulin (Sigma) second antibody. The anti-biotin antibody-secreting hybridomas were subcloned three or more times by limiting dilution to establish stable cell lines. The hybridoma cells were introduced into 2,6,10,14-tetramethyl pentadecane (pristane, Sigma)-primed peritoneal cavity of Balb/c mice to produce mAb-enriched ascites fluids.

The immunoglobulin subclass of the mAbs was determined by a sandwich ELISA using a mouse immunoglobulin isotyping kit.

ELISA Titrations

Biotin-BSA conjugate was immobilized on microtiter plates. After washing and blocking the plastic surface with 1% BSA and 0.05% Tween-20, the immobilized antigen was incubated with serial dilutions of the anti-biotin mAbs or HRP-streptavidin control. Following washes to remove the unbound anti-biotin antibody, the plates were further incubated with HRP-conjugated second antibody. The assay was continued with the HRP-streptavidin control plate with washes and $H_2O_2$-ABTS substrate reaction. A415 nm curve for each assay well was recorded by an automated microplate reader.

Reactivity with free biotin was determined using competition ELISA with biotin-BSA coated on the microplate and serial dilution of free biotin added to pre-determined concentrations of anti-biotin mAb or HRP-streptavidin control. The following ELISA procedure was as described above.

Items

Item 1. An isolated antibody or antigen binding fragment thereof which specifically binds to biotin of a biotin conjugate, and which has a higher affinity for biotin of a biotin conjugate than for free biotin.

Item 2. The isolated antibody or antigen binding fragment thereof of item 1, wherein the isolated antibody or antigen binding fragment thereof is an isolated monoclonal antibody or antigen binding fragment thereof.

Item 3. The isolated antibody or antigen binding fragment thereof of any one of item 1 or 2, further comprising an attached detectable label.

Item 4. The isolated antibody or antigen binding fragment thereof of any one of items 1 to 3, immobilized on a solid or semi-solid support.

Item 5. The isolated antibody or antigen binding fragment thereof of any one of items 1 to 4, comprising a heavy chain variable region 1 selected from the group consisting of: SEQ ID NO: 1, SEQ ID NO:3, SEQ ID NO:5, and a variant of any one of SEQ ID NO: 1, SEQ ID NO:3, SEQ ID NO:5.

Item 6. The isolated antibody or antigen binding fragment thereof of any one of items 1 to 5, comprising a heavy chain variable region 1 encoded by a nucleotide sequence selected from the group consisting of: SEQ ID NO: 7, SEQ ID NO:9, SEQ ID NO:11, and a variant of any one of SEQ ID NO: 7, SEQ ID NO:9, SEQ ID NO:11.

Item 7. The isolated antibody or antigen binding fragment thereof of any one of items 1 to 6, comprising a light chain variable region 1 selected from the group consisting of: SEQ ID NO: 2, SEQ ID NO:4, SEQ ID NO:6, and a variant of any one of SEQ ID NO: 2, SEQ ID NO:4, SEQ ID NO:6.

Item 8. The isolated antibody or antigen binding fragment thereof of any one of items 1 to 7, comprising a light chain variable region 1 encoded by a nucleotide sequence selected from the group consisting of: SEQ ID NO: 8, SEQ ID NO:10, SEQ ID NO:12, and a variant of any one of SEQ ID NO: 8, SEQ ID NO:10, or SEQ ID NO:12.

Item 9. The isolated antibody or antigen binding fragment thereof of any one of items 1 to 8 comprising a variant of heavy chain variable region 1 encoded by a nucleotide sequence which hybridizes to the complement of SEQ ID NO: 7, SEQ ID NO:9, or SEQ ID NO:11, respectively, under stringent hybridization conditions.

Item 10. The isolated antibody or antigen binding fragment thereof of any one of items 1 to 9 comprising a variant of light chain variable region 1 encoded by a nucleotide sequence which hybridizes to the complement of SEQ ID NO: 8, SEQ ID NO:10, or SEQ ID NO:12, respectively, under stringent hybridization conditions.

Item 11. The isolated antibody or antigen binding fragment thereof of any one of items 1 to 10 comprising a heavy chain variable region 1 of SEQ ID NO:1 or a variant thereof, a light chain variable region 1 of SEQ ID NO:2 or a variant thereof.

Item 12. The isolated antibody or antigen binding fragment thereof of any one of items 1 to 10 comprising a heavy chain variable region 1 of SEQ ID NO:3 or a variant thereof, a light chain variable region 1 of SEQ ID NO:4 or a variant thereof.

Item 13. The isolated antibody or antigen binding fragment thereof of any one of items 1 to 10 comprising a heavy chain variable region 1 of SEQ ID NO:5 or a variant thereof, a light chain variable region 1 of SEQ ID NO:6 or a variant thereof.

Item 14. A hybridoma cell comprising a nucleic acid encoding a monoclonal antibody according to any one of items 1 to 13.

Item 15. A method for detecting a biotin conjugate in a sample, comprising: contacting a sample containing or suspected of containing a biotin conjugate with an anti-biotin antibody and/or antigen binding fragment thereof of any one of items 1 to 13, under binding conditions; and detecting binding of the anti-biotin antibody and/or antigen binding fragment thereof with the biotin conjugate.

Item 16. The method of item 15, wherein the method comprises an ELISA.

Item 17. The method of item 15, wherein the method comprises immunochromatography; antigen capture; flow cytometry; immunoblot;

immunofluorescence; immunoprecipitation; immunodiffusion; competitive immunoassay, immunocytochemistry; radioimmunoassay; and combinations of any of these.

Item 18. An immunoassay kit, comprising: one or more antibodies or antigen binding fragments of any of items 1 to 13, and/or the hybridoma cell of item 14.

Item 19. An immunoassay kit using the method of any of items 15 to 17, for analysis of biological samples avoiding interference of free biotin such as that in blood samples from human subjects who take biotin as a medical therapy or nutritional supplement.

Item 20. An isolated antibody or antigen binding fragment thereof substantially as described or shown herein.

Item 21. A method for detecting a biotin conjugate in a sample substantially as described or shown herein.

Item 22. An immunoassay kit substantially as described or shown herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An isolated monoclonal antibody or antigen binding fragment thereof which specifically binds to biotin of a biotin conjugate, and which has a higher affinity for biotin of a biotin conjugate than for free biotin, wherein the antibody comprises one of the sets of variable heavy and light chain regions:
   a) a heavy chain variable region comprising the amino acid sequence of SEQ ID NO:1 and a light chain variable region comprising the amino acid sequence of SEQ ID NO:2;
   b) a heavy chain variable region comprising the amino acid sequence of SEQ ID NO:3 and a light chain variable region comprising the amino acid sequence of SEQ ID NO:4; or
   c) a heavy chain variable region comprising the amino acid sequence of SEQ ID NO:5 and a light chain variable region comprising the amino acid sequence of SEQ ID NO:6.

2. The isolated monoclonal antibody or antigen binding fragment thereof of claim 1, further comprising an attached detectable label.

3. The isolated monoclonal antibody or antigen binding fragment thereof of claim 1, immobilized on a solid or semi-solid support.

4. The isolated monoclonal antibody or antigen binding fragment thereof of claim 1, wherein:
   a) the heavy chain variable region is encoded by the nucleotide sequence of SEQ ID NO: 7, and the light chain variable region is encoded by the nucleotide sequence of SEQ ID NO: 8;
   b) the heavy chain variable region is encoded by the nucleotide sequence of SEQ ID NO: 9, and the light chain variable region is encoded by the nucleotide sequence of SEQ ID NO: 10; or
   c) the heavy chain variable region is encoded by the nucleotide sequence of SEQ ID NO: 11, and the light chain variable region is encoded by the nucleotide sequence of SEQ ID NO: 12.

5. A hybridoma cell comprising a nucleic acid encoding the monoclonal antibody or an antigen binding fragment thereof according to claim 1.

6. A method for detecting a biotin conjugate in a sample, comprising:
   contacting a sample containing or suspected of containing a biotin conjugate with the monoclonal anti-biotin antibody or antigen binding fragment thereof of claim 1, under binding conditions; and
   detecting binding of the monoclonal anti-biotin antibody or antigen binding fragment thereof with the biotin conjugate.

7. The method of claim 6, wherein the method comprises an ELISA.

8. The method of claim 6, wherein the method comprises immunochromatography; antigen capture; flow cytometry; immunoblot; immunofluorescence; immunoprecipitation; immunodiffusion; competitive immunoassay, immunocytochemistry; radioimmunoassay; and combinations of any of these.

9. The method of claim 6, wherein the sample is a blood sample from a human subject who takes biotin as medical therapy or nutritional supplement.

10. An immunoassay kit, comprising the monoclonal antibody or antibody binding fragment thereof of claim 1.

11. An immunoassay kit, comprising the hybridoma cell of claim 5.

* * * * *

SEQUENCE LISTING

<160> NUMBER OF SEQ ID NOS: 16

<210> SEQ ID NO 1
<211> LENGTH: 110
<212> TYPE: PRT
<213> ORGANISM: Mus musculus

<400> SEQUENCE: 1

Gly Glu Thr Val Lys Ile Ser Cys Lys Ala Ser Gly Tyr Thr Phe Ile
1               5                   10                  15

Asn Phe Gly Met Asn Trp Val Lys Gln Ala Pro Gly Lys Gly Leu Lys
            20                  25                  30

Trp Met Gly Trp Ile Asn Pro Tyr Thr Gly Glu Pro Thr Tyr Ala Asp
        35                  40                  45

Asp Phe Lys Gly Arg Phe Ala Phe Ser Leu Glu Thr Ser Ala Ser Thr
    50                  55                  60

Ala Tyr Leu Gln Ile Asp Asn Leu Lys Asn Glu Asp Thr Ala Thr Tyr
65                  70                  75                  80

Phe Cys Ala Arg Ser Gly Trp Glu Asn Pro Tyr Trp Gly Gln Gly Thr
                85                  90                  95

Leu Val Thr Val Ser Ala Ala Lys Thr Thr Pro Pro Ser Val
            100                 105                 110

<210> SEQ ID NO 2
<211> LENGTH: 105
<212> TYPE: PRT
<213> ORGANISM: Mus musculus

<400> SEQUENCE: 2

Gly Asp Gln Ala Ser Ile Ser Cys Arg Ser Ser Gln Arg Leu Val Tyr
1               5                   10                  15

Ser Asn Gly Asn Thr Tyr Leu His Trp Tyr Leu Gln Lys Pro Gly Gln
            20                  25                  30

Ser Pro Lys Leu Leu Ile Tyr Lys Val Ser Asn Arg Phe Ser Gly Val
        35                  40                  45

Pro Asp Arg Phe Ser Gly Ser Gly Ser Gly Thr Asp Phe Thr Leu Lys
    50                  55                  60

Ile Ser Arg Val Lys Ala Glu Asp Leu Gly Val Tyr Phe Cys Ser Gln
65                  70                  75                  80

Ser Thr His Val Pro Trp Thr Phe Gly Gly Gly Thr Lys Leu Glu Ile
                85                  90                  95

Lys Arg Ala Asp Ala Ala Pro Thr Val
            100                 105

<210> SEQ ID NO 3
<211> LENGTH: 112
<212> TYPE: PRT
<213> ORGANISM: Mus musculus

<400> SEQUENCE: 3

Ala Gly Gly Pro Glu Leu Ser Cys Ala Ala Ser Gly Phe Thr Phe Ser
1               5                   10                  15

Ser Tyr Ala Met Ser Trp Val Arg Gln Thr Pro Glu Lys Arg Val Glu
            20                  25                  30

Trp Val Ala Ser Ile Leu Ser Gly Gly Tyr Ile Tyr Tyr Ser Asp Ser
        35                  40                  45

Met Arg Gly Arg Phe Thr Ile Ser Arg Asp Asn Ala Arg Asn Ile Leu
    50                  55                  60

Tyr Leu Gln Met Ser Ser Leu Arg Ser Glu Asp Thr Ala Met Tyr Tyr
65                  70                  75                  80

Cys Ser Arg Gly Gln Ser Gly Thr Val Phe Phe Asp Tyr Trp Gly Gln
                85                  90                  95

Gly Thr Thr Leu Thr Val Ser Ser Ala Lys Thr Thr Pro Pro Ser Val
            100                 105                 110

<210> SEQ ID NO 4
<211> LENGTH: 98
<212> TYPE: PRT
<213> ORGANISM: Mus musculus

<400> SEQUENCE: 4

Ala Val Val Thr Gln Glu Ser Ala Leu Thr Thr Ser Pro Gly Gly Thr
1               5                   10                  15

Val Ile Leu Thr Cys Arg Ser Ser Thr Gly Ala Val Thr Thr Ser Asn
                20                  25                  30

Tyr Ala Asn Trp Val Gln Glu Lys Pro Asp His Leu Phe Thr Gly Leu
            35                  40                  45

Ile Gly Gly Thr Ser Asn Arg Gly Pro Gly Val Pro Val Arg Phe Ser
50                  55                  60

Gly Ser Leu Ile Gly Asp Lys Ala Ala Leu Thr Ile Thr Gly Ala Gln
65                  70                  75                  80

Thr Glu Asp Asp Ala Met Tyr Phe Cys Ala Leu Trp Tyr Asn Thr His
                85                  90                  95

Tyr Val

<210> SEQ ID NO 5
<211> LENGTH: 117
<212> TYPE: PRT
<213> ORGANISM: Mus musculus

<400> SEQUENCE: 5

Gly Gly Ser Leu Arg Leu Ser Cys Ala Thr Ser Gly Phe Thr Phe Thr
1               5                   10                  15

Asp Tyr Tyr Met Asn Trp Val Arg Gln Pro Pro Gly Lys Ala Leu Glu
                20                  25                  30

Trp Leu Gly Phe Ile Arg Asn Lys Ala Asn Gly Tyr Thr Thr Asp Tyr
            35                  40                  45

Ser Ala Ser Val Lys Gly Arg Phe Thr Ile Ser Arg Asp Asn Ser Gln
50                  55                  60

Ser Ile Leu Tyr Leu Gln Met Asn Thr Leu Arg Ala Glu Asp Ser Ala
65                  70                  75                  80

Thr Tyr Tyr Cys Ala Arg Asp Met Arg Gly Pro Gly Thr Ala Trp Phe
                85                  90                  95

Ala Tyr Trp Gly Gln Gly Thr Leu Val Thr Val Ser Ala Ala Lys Thr
            100                 105                 110

Thr Pro Pro Ser Val
            115

<210> SEQ ID NO 6
<211> LENGTH: 98
<212> TYPE: PRT
<213> ORGANISM: Mus musculus

<400> SEQUENCE: 6

Ala Val Val Thr Gln Glu Ser Ala Leu Thr Thr Ser Pro Gly Gly Thr

```
1               5                  10                 15
Val Ile Leu Thr Cys Arg Ser Ser Thr Gly Ala Val Thr Thr Ser Asn
            20                 25                 30

Tyr Ala Asn Trp Val Gln Glu Lys Pro Asp His Leu Phe Thr Gly Leu
            35                 40                 45

Ile Gly Gly Thr Ser Asn Arg Ala Pro Gly Val Pro Val Arg Phe Ser
        50                 55                 60

Gly Ser Leu Ile Gly Asp Lys Ala Ala Leu Thr Ile Thr Gly Ala Gln
65                  70                 75                 80

Thr Glu Asp Asp Ala Met Tyr Phe Cys Ala Leu Trp Tyr Ser Thr His
                85                 90                 95

Cys Ser
```

<210> SEQ ID NO 7
<211> LENGTH: 335
<212> TYPE: DNA
<213> ORGANISM: Mus musculus

<400> SEQUENCE: 7

```
agtcaagatc tcctgcaagg cttctggata taccttcata aactttggaa tgaactgggt    60
gaagcaggct ccaggaaagg gtttaaagtg gatgggctgg ataaacccct acactggaga   120
accaacatat gcggatgact caagggacg gtttgccttc tctttggaaa cctctgccag    180
cactgcctat ttgcagatcg acaacctcaa aaatgaggac acggctacat atttctgtgc   240
aagatccggg tgggaaaacc cttactgggg ccaagggact ctggtcactg tctctgcagc   300
caaaacgaca cccccatctg tctatagatc ttcca                              335
```

<210> SEQ ID NO 8
<211> LENGTH: 282
<212> TYPE: DNA
<213> ORGANISM: Mus musculus

<400> SEQUENCE: 8

```
agacttgtat acagtaatgg aaacacctat ttacattggt acctgcagaa gccaggccag    60
tctccaaaac tcctgatcta caaagtttcc aaccgatttt ctggggtccc agacaggttc   120
agtggcagtg gatcagggac agatttcaca ctcaagatca gcagagtgaa ggctgaggat   180
ctgggagttt attctgctc tcaaagtaca catgttccgt ggacgttcgg tggaggcacc    240
aagctggaaa tcaaacgggc tgatgctgca ccaactgtat cc                      282
```

<210> SEQ ID NO 9
<211> LENGTH: 325
<212> TYPE: DNA
<213> ORGANISM: Mus musculus

<400> SEQUENCE: 9

```
gaactctcct gtgcagcctc tggattcact ttcagtagtt atgccatgtc ttgggttcgc    60
cagactccag agaagagggt ggagtgggtc gcatccattc ttagtggtgg ttatatttat   120
tattcagaca gtatgagggg tcgattcacc atctccagag ataatgccag gaacatcctg   180
tacctgcaaa tgagcagtct gaggtctgag gacacggcca tgtattactg ttcaagaggc   240
caaagtggga cggttttttt tgactactgg ggccaaggca ccactctcac agtctcctca   300
gccaaaacga caccccatc tgtct                                          325
```

<210> SEQ ID NO 10

```
<211> LENGTH: 310
<212> TYPE: DNA
<213> ORGANISM: Mus musculus

<400> SEQUENCE: 10
gccgaacata atgggtgttg taccatagag cacagaaata cattgcatca tcctcagtct      60
gtgcccctgt gatggtgagg gcagccttgt ctccaatcag ggagcctgag aatctgacag     120
gaacacctgg acctcggttg ctggtaccac ctattagacc agtgaataaa tgatctggtt     180
tttcttggac ccagttggca tagttactag ttgtaacagc cccagtactt gagcgacaag     240
tgagtatgac tgttccacca ggtgatgtgg tgagtgcaga ttcctgagtc acaacagcct     300
ggcatgcacc                                                            310

<210> SEQ ID NO 11
<211> LENGTH: 349
<212> TYPE: DNA
<213> ORGANISM: Mus musculus

<400> SEQUENCE: 11
gggggttctc tgagactctc ctgtgcaact tctgggttca ccttcactga ttactacatg      60
aactgggtcc gccagcctcc aggaaaggca cttgagtggt tgggttttat tagaaacaaa     120
gcaaatggtt acacaacaga ctacagtgca tctgtgaagg gtcggttcac catctccaga     180
gataattccc aaagcatcct ctatcttcaa atgaataccc tgcgagctga agacagtgcc     240
acttattact gtgcaagaga tatgaggggg cctgggacgg cctggtttgc ttactggggc     300
caagggactc tggtcactgt ctctgcagcc aaaacgacac ccccatctg                 349

<210> SEQ ID NO 12
<211> LENGTH: 290
<212> TYPE: DNA
<213> ORGANISM: Mus musculus

<400> SEQUENCE: 12
caatgggtgc tgtaccatag agcacagaaa tacattgcat catcctcagt ctgtgcccct      60
gtgatggtga gggcagcctt gtctccaatc agggagcctg agaatctgac aggaacacct     120
ggagctcggt tgctggtacc acctattaga ccagtgaata atgatctggt tttttcttgg     180
acccagttgg catagttact agttgtaaca gccccagtac ttgagcgaca agtgagtatg     240
actgttccac caggtgatgt ggtgagtgca gattcctgag tcacaacagc                290

<210> SEQ ID NO 13
<211> LENGTH: 104
<212> TYPE: PRT
<213> ORGANISM: Mus musculus

<400> SEQUENCE: 13

Ser Gln Ser Leu Ser Ile Thr Cys Thr Val Ser Gly Phe Ser Leu Thr
1               5                   10                  15

Ala Tyr Gly Val Asp Trp Val Arg Gln Pro Pro Gly Lys Gly Leu Glu
            20                  25                  30

Trp Leu Gly Val Ile Trp Gly Gly Gly Arg Thr Asn Tyr Asn Ser Gly
        35                  40                  45

Leu Met Ser Arg Leu Ser Ile Arg Lys Asp Asn Ser Lys Ser Gln Val
    50                  55                  60

Phe Leu Thr Met Asn Ser Leu Gln Thr Asp Asp Thr Ala Lys Tyr Tyr
65                  70                  75                  80
```

```
Cys Val Lys His Thr Asn Trp Asp Gly Gly Phe Ala Tyr Trp Gly Gln
                 85                  90                  95

Gly Thr Thr Val Thr Val Ser Ser
            100
```

<210> SEQ ID NO 14
<211> LENGTH: 112
<212> TYPE: PRT
<213> ORGANISM: Mus musculus

<400> SEQUENCE: 14

```
Gly Ala Glu Leu Val Arg Pro Gly Thr Ser Val Lys Val Ser Cys Lys
1               5                   10                  15

Ala Phe Gly Tyr Ala Phe Ser Asn Tyr Leu Ile Glu Trp Val Gln Gln
                20                  25                  30

Arg His Gly Gln Gly Leu Glu Gly Ile Gly Val Met Ile Tyr Pro Gly
            35                  40                  45

Ser Gly Asp His Lys Tyr Asn Glu Lys Phe Lys Gly Lys Ala Thr Leu
    50                  55                  60

Thr Ala Asp Lys Ser Ser Ser Thr Ala Tyr Met Gln Leu Ser Ser Leu
65                  70                  75                  80

Thr Ser Asp Asp Ser Ala Val Tyr Phe Cys Ala Arg Phe Asp Tyr Asp
                85                  90                  95

Val Thr Tyr Ala Met Ala Tyr Trp Gly Gln Gly Thr Ser Ala Thr Val
            100                 105                 110
```

<210> SEQ ID NO 15
<211> LENGTH: 96
<212> TYPE: PRT
<213> ORGANISM: Mus musculus

<400> SEQUENCE: 15

```
Glu Lys Val Thr Met Ser Cys Lys Ser Gln Ser Leu Leu Asn Ser
1               5                   10                  15

Arg Thr Arg Lys Asn Tyr Leu Ala Trp Tyr Gln Gln Lys Pro Gly Gln
                20                  25                  30

Ser Pro Lys Leu Leu Ile Tyr Trp Ala Ser Ser Arg Glu Ser Gly Val
            35                  40                  45

Pro Asp Arg Phe Thr Gly Ser Gly Ser Gly Thr Asp Phe Thr Leu Thr
    50                  55                  60

Ile Ser Ser Val Gln Ala Glu Asp Leu Ala Val Tyr Tyr Cys Lys Gln
65                  70                  75                  80

Ser Tyr Asn Leu Tyr Thr Phe Gly Gly Gly Thr Lys Leu Glu Ile Lys
                85                  90                  95
```

<210> SEQ ID NO 16
<211> LENGTH: 98
<212> TYPE: PRT
<213> ORGANISM: Mus musculus

<400> SEQUENCE: 16

```
Ala Val Val Thr Gln Glu Ser Ala Leu Thr Thr Ser Pro Gly Glu Thr
1               5                   10                  15

Val Thr Leu Thr Cys Arg Ser Ser Thr Gly Ala Val Thr Ile Ser Asn
                20                  25                  30

Tyr Ala Asn Trp Val Gln Glu Lys Pro Asp Tyr Leu Phe Thr Gly Leu
            35                  40                  45

Ile Gly Gly Thr Asn Asn Arg Ala Pro Gly Val Pro Ala Arg Phe Ser
```

-continued

```
                50                  55                  60
Gly Ser Leu Ile Gly Asp Lys Ala Ala Leu Thr Ile Thr Gly Ala Gln
65                  70                  75                  80

Thr Glu Asp Glu Ala Met Tyr Phe Cys Val Leu Trp Tyr Ser Asn His
                85                  90                  95

Trp Val
```